United States Patent [19]

Gainutdinova et al.

[11] Patent Number: 4,841,991

[45] Date of Patent: Jun. 27, 1989

[54] INTRAUTERINE CONTRACEPTIVE DEVICE

[75] Inventors: Raisa V. Gainutdinova; Vera M. Petrova; Alevtina I. Blokhina; Boris S. Fridman; Pinkhos U. Gamer, all of Kazan, U.S.S.R.

[73] Assignee: Nauchno-Proizvodstvennoe Obiedinenie "Medinstrument", Kazan, U.S.S.R.

[21] Appl. No.: 91,944

[22] Filed: Sep. 1, 1987

[51] Int. Cl.[4] .................... A61F 5/46

[52] U.S. Cl. .................... 128/833; 128/839

[58] Field of Search .................... 128/130, 833, 839

[56] References Cited

U.S. PATENT DOCUMENTS

| | | | |
|---|---|---|---|
| 3,405,711 | 10/1968 | Bakunin | 128/130 |
| 3,457,915 | 7/1969 | Eshelman | 128/130 |
| 3,576,186 | 4/1971 | Robinson | 128/130 |
| 3,937,217 | 2/1976 | Kosonen | 128/130 |
| 4,200,091 | 4/1980 | Del Conte | 128/130 |
| 4,553,536 | 11/1985 | Chiozza | 128/130 |
| 4,628,924 | 12/1986 | Cimber | 128/130 |

FOREIGN PATENT DOCUMENTS

| | | | |
|---|---|---|---|
| 117818 | 9/1984 | France | 128/130 |
| 1456746 | 11/1976 | United Kingdom . | |

OTHER PUBLICATIONS

Nova T Cu200Ag (A/O Huhtamaki, Leiras, Finland).

*Primary Examiner*—Robert A. Hafer
*Assistant Examiner*—Charles H. Sam
*Attorney, Agent, or Firm*—Fleit, Jacobson, Cohn, Price, Holman & Stern

[57] ABSTRACT

An intrauterine contraceptive device, comprising a strip with rounded-off ends, a rod connected to the strip to form a T-shaped element therewith, a fixing element for retaining the entire device in the uterine cavity, made as an elastic loop, and a coil fitted over the rod, the elastic loop of the fixing element having an arc-shaped base and two elastic arms connected to the base and secured to the strip at the base of the rod, which elastic loop is coplanar with the rod and strip and encompasses the rod.

3 Claims, 1 Drawing Sheet

1
7
5
3
2
6

INTRAUTERINE CONTRACEPTIVE DEVICE

FIELD OF THE INVENTION

This invention relates generally to contraceptive devices and more specifically, to intrauterine devices (IUD).

The invention is applicable in gynecological practice for prevention of an undesirable pregnancy in women with diversely sized and shaped uterine cavity, as well as a prevention measure aimed at birth control and family planning.

BACKGROUND OF THE INVENTION

One state-of-the-art intrauterine device (cf. GB, B, No. 1,456,46) is known to be made as a T-shaped element, comprising a rod and two elastic arms branching off radially therefrom, and an elastic loop provided at its end. The arms are equally curved, the radius of curvature of each arm being adequately large, while the angle between the rod and each of the arms is less than 90 degrees.

The prior-art device is characterized by the fact that an inadequately intimate contact between the arms of the device and the mucous membrane of the uterine fundus effects adversely the contraceptive effect, while insufficient elasticity and size of the loop are liable to inflict trauma and irritate the mucosa of the internal uterine orifice and hence spontaneous expulsion of the device.

Another prior-art intrauterine device, i.e. Nova T Cu200Ag (A/O Huhtamaki, Leiras, Finland) is known to comprise a rod with a copper coil, a strip with the rounded-off ends, held to the rod so as form a T-shaped element therewith, and a fixing element to retain the entire device within the uterine cavity, said fixing element being in fact an elastic loop located at the rod end.

The aforesaid prior-art device is characterized by the fact that provision of the elastic loop at the rod end, the loop size and shape fail to provide constant pressing of the strip against the mucous membrane of the uterine fundus, which is the cause of impaired contraceptive effect. On the other hand the base of the elastic loop irritates the receptors of the mucosa in the region of the internal uterine orifice, provokes extraordinary contractions of the uterine muscle and promotes expulsion of the entire device.

In addition, the devices discussed above should have various sizes and shapes to suite the various sizes and shapes of the uterine cavity.

SUMMARY OF THE INVENTION

It is an object of the invention to provide better contraceptive effect.

It is another object of the invention to reduce traumatic lesion of the uterine cavity mucosa.

It is one more object of the invention to provide reliable fixing of the intrauterine device within the uterine cavity.

It is still more object of the invention to render the occurrence of expulsion less frequent.

Said objects can be carried into effect in an intrauterine contraceptive device, comprising a strip with the rounded-off ends, a rod connected to the strip to form a T-shaped element, a fixing element adapted to retain the entire device in the uterine cavity and shaped as an elastic loop, and a coil fitted on the rod, wherein according to the invention, the elastic loop of the fixing element has an arc-shaped base and two elastic arms connected thereto and held to the strip at the base of the rod, said loop being coplanar with the rod and strip, and encompassing the rod.

It is also expedient that in the intrauterine contraceptive device of the invention the arc-shaped base of the elastic loop have a thickened portion aimed at establishing a support located over the uterine cervix.

The intrauterine contraceptive device carried into effect in a way described above, provides for a constant pressing of the strip against the mucous membrane of the uterine fundus in an uterus of any size, shape and position, this being due to springiness of the fixing element consisting of a thickened arc-shaped base and elastic arms. All this makes it possible to attain the high contraceptive effect.

Apart from that, the construction of the fixing element, that is, the thickened arc-shaped base of the elastic loop prevents the device from penetrating into the region of the internal uterine orifice and is situated above that region so as not to inflict trauma upon the mucosal receptors and hence to ensure against expulsion of the entire device.

BRIEF DESCRIPTION OF THE DRAWINGS

In what follows the invention will become more apparent from consideration of a specific embodiment thereof with reference to the accompanying drawings, wherein.

DETAILED DESCRIPTION OF THE INVENTION

Figure 1:
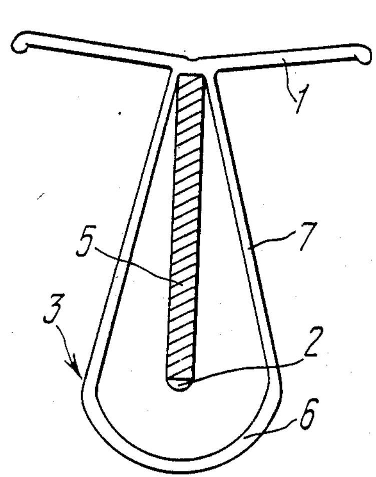
FIG. 1 is a general schematic view of an intrauterine contraceptive device, according to the invention.
Figure 2:
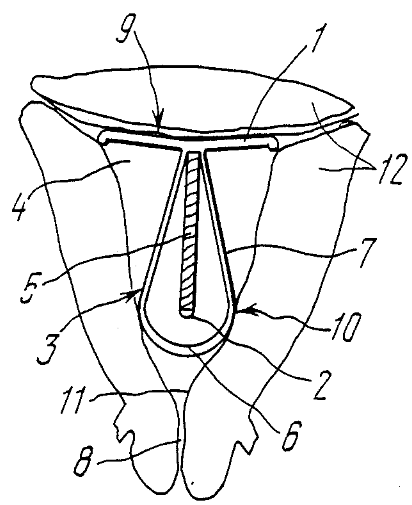
FIG. 2 is a view of the intrauterine device of FIG. 1 when inserted into the cavity of a uterus having the normal shape and size, the so-called "ideal variant", according to the invention.

The intrauterine contraceptive device of the invention comprises a strip 1 (FIGS. 1, 2) having rounded-off ends, a rod 2 connected to the strip 1 so as to establish a T-shaped element therewith, a fixing element 3 adapted to retain the entire device in a uterine cavity 4 and shaped as an elastic loop, and a coil 5 fitted over the rod 2. The elastic loop of the fixing element 3 has an arc-shaped base 6 having a thickened portion, and two elastic arms 7 connected to the base 6 and held to the strip 1 at the base of the rod 2. The elastic loop of the fixing element 3 is coplanar with the rod 2 and the strip 1, and encompasses the rod 2.

Figure 3:
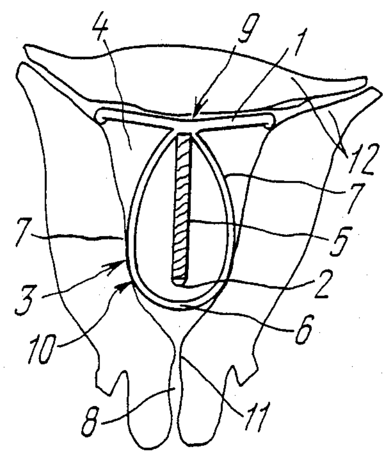
FIG. 3 shows the intrauterine device of FIG. 1 when inserted into the cavity of a uterus featuring an increased transversal dimensions, according to the invention.

The intrauterine contraceptive device of the invention is to be inserted into the uterine cavity 4 (FIG. 2) through a cervical canal 8 of the uterus with the aid of a special syringe (omitted in the Drawing), and is so positioned that the strip 1 be in contact with a mucous membrane 9 of the uterine fundus, whereas the arc-shaped thickened base 6 of the fixing element 3 should rest against uterine walls 10 an adequate distance from the region of a uterine cervic 11. Whenever the intrauterine device has to be inserted into the uterine cavity 4 featuring an increased transversal dimension, i.e., a shortened uterine body (FIG. 3), the fixing element 3 gets shortened under the action of the spring effect thereof, thus keeping the strip 1 in an intimate contact with the mucous membrane 9 of the uterine fundus.

Figure 4:
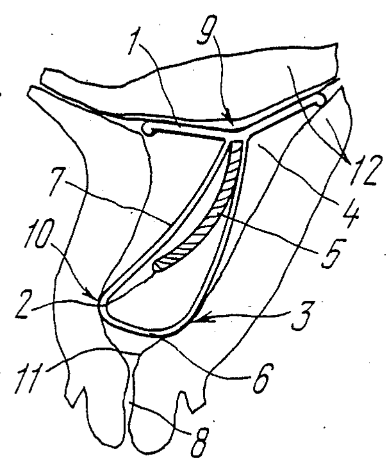
FIG. 4 illustrates the intrauterine device of FIG. 1 when inserted into the cavity of a uterus having an increased longitudinal dimension and an irregular shape, according to the invention.

Whenever the intrauterine device has to be inserted into the uterine cavity 4 featuring an elongated body and irregular shape (FIG. 4), the fixing element 3 becomes elongated under the action of the spring effect and assumes the irregular shape to suit that of the uterus involved. As a result, the strip 1 is tightly pressed to the mucous membrane 9 of the uterine fundus.

Proceeding from all described above the aforedisclosed intrauterine device may be considered as versatile and producing an adequate contraceptive effect so that a single size and type is equally applicable in diversely shaped, sized and positioned uteri.

Better contraceptive effect is attained in the aforesaid device due to the spring action produced by the fixing element 3. As a result, the strip 1 of the device is in a constant intimate contact with the mucosa 9 of the uterine fundus, thus exerting a mechanical action on the uterus.

The thickened arc-shaped base 6 of the elastic fixing element 3 contributes to reliable fixation of the intrauteral device in the uterine cavity 4 above the uterine cervix 11 thus preventing the device from expulsion.

What is claimed is:

1. An intrauterine contraceptive device, comprising:

a strip with rounded-off ends;

a rod connected to said strip to form a Tshaped element;

a coil fitted over said rod;

a fixing elment for retaining the entire device in the uterine cavity, shaped as an elastic loop coplanar with said rod and said strip and encompassing said rod, said loop having an arc-shaped base and two elastic arms connected to said arc-shaped base, said arms being held to said strip at the base of said rod.

2. An intrauterine contraceptive device, according to claim 1 wherein said arc-shaped base of said fixing element is thickened so as to establish a support above the uterine cervix.

3. An intrauterine contraceptive device, consisting essentially of:

a strip having rounded ends;

a rod having a base connected to said strip intermediate said rounded ends of said strip to form a T-shaped element;

a coil fitted over said rod; and a fixing element for retaining the entire intrauterine contraceptive device in a uterine cavity, said fixing element being shaped as an elastic loop coplanar with said rod and said strip, said elastic loop having an arc-shaped base and two elastic arms extending from said arc-shaped base, said elastic arms being fixed to said strip at the base of said rod, said fixing element encompassing said rod such that the end of said rod opposite the base does not extend beyond the arc-shaped base of said fixing element.

* * * * *